(12) United States Patent
Cataltepe

(10) Patent No.: US 10,646,690 B2
(45) Date of Patent: May 12, 2020

(54) FLEXIBLE SURGICAL SHEATH AND MULTI-PART INSERTION CANNULA

(71) Applicant: Oguz I. Cataltepe, Weston, MA (US)

(72) Inventor: Oguz I. Cataltepe, Weston, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/682,115

(22) Filed: Nov. 20, 2012

(65) Prior Publication Data

US 2014/0142394 A1    May 22, 2014

(51) Int. Cl.
   *A61B 17/34* (2006.01)
   *A61M 25/01* (2006.01)
   *A61B 17/02* (2006.01)

(52) U.S. Cl.
   CPC ..... *A61M 25/0102* (2013.01); *A61B 17/0218* (2013.01); *A61B 17/3431* (2013.01); *A61B 17/3439* (2013.01); *A61B 17/0293* (2013.01)

(58) Field of Classification Search
   CPC ....... A61B 17/0218; A61B 1/32; A61B 17/02; A61B 17/0206; A61B 17/0293; A61B 17/3423; A61B 2017/0256; A61B 19/5202; A61B 17/3421; A61B 17/3431; A61M 25/0102; A61M 29/00
   USPC .................................................. 600/201–246
   See application file for complete search history.

(56) References Cited

U.S. PATENT DOCUMENTS

| | | | | |
|---|---|---|---|---|
| 3,841,317 A | * | 10/1974 | Awais | 600/203 |
| 4,690,132 A | * | 9/1987 | Bayer et al. | 600/219 |
| 5,125,396 A | * | 6/1992 | Ray | 600/208 |
| 5,391,156 A | * | 2/1995 | Hildwein | A61B 17/29 411/503 |
| 5,967,970 A | * | 10/1999 | Cowan et al. | 600/207 |
| 5,976,146 A | * | 11/1999 | Ogawa | A61B 17/00234 604/174 |
| 6,096,046 A | * | 8/2000 | Weiss | 606/119 |
| 6,159,179 A | * | 12/2000 | Simonson | 604/117 |
| 6,171,282 B1 | * | 1/2001 | Ragsdale | A61B 17/3423 604/164.11 |

(Continued)

OTHER PUBLICATIONS

Yadav, et al., A New Minimally Invasive Tubular Brain Retractor System for Surgery of Deep Intracerebral Hematoma, Neurology India, vol. 59, No. 1, Jan.-Feb. 2011, pp. 74-77, printed from Bioline International Website Mar. 21, 2012, http://www.bioline.org.

*Primary Examiner* — Jacqueline T Johanas
(74) *Attorney, Agent, or Firm* — Millstein Zhang & Wu LLC

(57) ABSTRACT

A flexible surgical sheath and multi-part insertion cannula for inserting the flexible sheath in a cranial surgical tunnel for gaining access to a ventricle or other surgical target. An obturator or other elongated insertion member drives a sheath assembly into a surgical recess, typically a hole drilled through the skull and brain of the surgical patient. The inserted sheath assembly includes two or more rigid sheath portions disposed around the obturator. The obturator has a tapered or angled tip for guiding the sheath assembly through the surgical tunnel to a target region such as a ventricle or other brain structure for which surgical intervention is sought. Following insertion, the obturator is withdrawn and a flexible sheath inserted in an insertion tunnel defined by the rigid sheath portions.

10 Claims, 19 Drawing Sheets

(56) References Cited

U.S. PATENT DOCUMENTS

| | | | |
|---|---|---|---|
| 6,354,995 B1* | 3/2002 | Hoftman et al. | 600/219 |
| 6,428,473 B1* | 8/2002 | Leonard et al. | 600/219 |
| 7,179,225 B2* | 2/2007 | Shluzas et al. | 600/219 |
| 7,189,249 B2* | 3/2007 | Hart | A61B 17/34 604/264 |
| 7,261,688 B2* | 8/2007 | Smith et al. | 600/210 |
| 7,850,608 B2* | 12/2010 | Hamada | 600/219 |
| 9,421,034 B2* | 8/2016 | Hart | A61B 17/0293 |
| 2003/0073934 A1* | 4/2003 | Putz | A61M 25/0668 600/585 |
| 2006/0004408 A1* | 1/2006 | Morris | A61B 17/0057 606/215 |
| 2006/0106416 A1* | 5/2006 | Raymond et al. | 606/198 |
| 2006/0149137 A1* | 7/2006 | Pingleton | A61B 1/32 600/208 |
| 2006/0200003 A1* | 9/2006 | Youssef | 600/207 |
| 2006/0212062 A1* | 9/2006 | Farascioni | A61B 17/3439 606/191 |
| 2006/0247499 A1* | 11/2006 | Butler et al. | 600/208 |
| 2006/0287583 A1* | 12/2006 | Mangiardi | 600/208 |
| 2007/0038034 A1* | 2/2007 | Sweeney, II | 600/219 |
| 2008/0109026 A1 | 5/2008 | Kassam | |
| 2008/0132764 A1* | 6/2008 | Hamada | 600/201 |
| 2008/0132766 A1* | 6/2008 | Dant et al. | 600/219 |
| 2009/0312611 A1* | 12/2009 | Mangiardi | 600/210 |
| 2010/0217090 A1* | 8/2010 | Heiges et al. | 600/217 |
| 2010/0249524 A1* | 9/2010 | Ransden | A61B 17/3423 600/207 |
| 2010/0292532 A1* | 11/2010 | Kadykowski et al. | 600/104 |
| 2011/0082342 A1* | 4/2011 | Whitman et al. | 600/206 |
| 2011/0144448 A1* | 6/2011 | Shelton, IV | A61B 17/3423 600/216 |
| 2012/0157783 A1* | 6/2012 | Okoniewski | A61B 17/3423 600/208 |
| 2013/0274557 A1* | 10/2013 | Bowman | A61B 17/0206 600/202 |
| 2014/0171873 A1* | 6/2014 | Mark | A61B 17/3417 604/164.06 |

\* cited by examiner

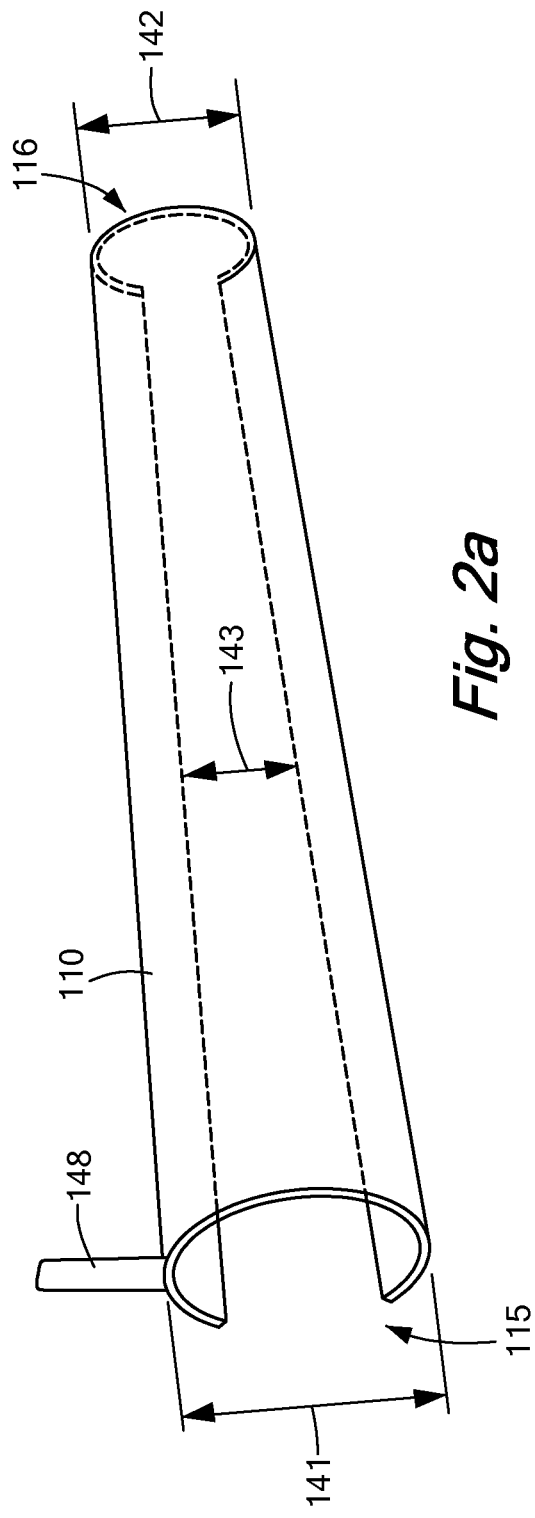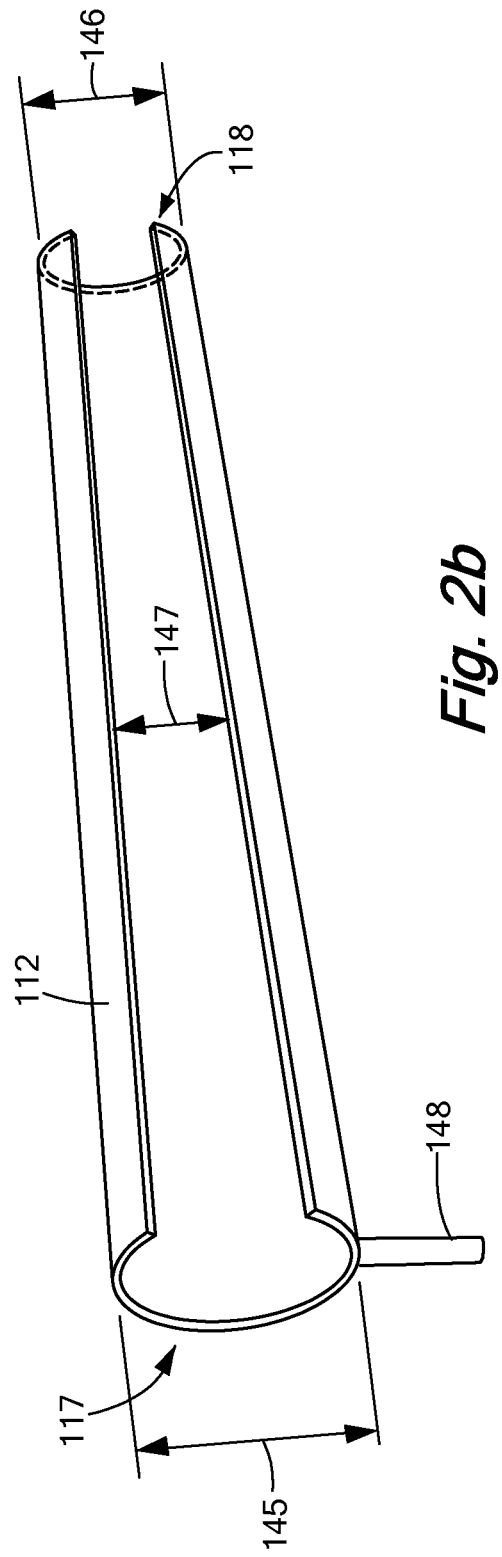

FLEXIBLE SURGICAL SHEATH AND MULTI-PART INSERTION CANNULA

BACKGROUND

Neurosurgical techniques involve precise manipulations in confined spaces. For surgical procedures in the brain, precision is particularly important due to the density of neurological structures. Further, the relative sensitivity of brain tissue, coupled with the potential severity of degraded tissue, make precise procedures that minimize collateral effects to surrounding tissue of utmost importance. In recent decades, usage of endoscopic surgical instruments have gained popularity over traditional procedures which removed a portion of the skull for open access.

Minimally invasive procedures using endoscopic techniques employ narrow, elongated instruments through smaller incisions, rather than open techniques. Surgical procedures with endoscopic techniques have been mostly performed for intraventricular procedures in the brain. There are many types of endoscopes which generally share some common features: light source, lens system, attached camera and working channels to introduce the surgical instruments. For example, a craniotomy is surgical procedure where a small opening is made in the skull to gain access to a tumor. The craniotomy is the fundamental technique used in tumor resection. It involves making an incision in the patient's scalp and then an opening in the skull. This is done using specialized endoscopic drills. Such an opening allows access to the intracranial cavity where the brain and ventricle are located.

SUMMARY

Neurosurgical procedures involving the brain tend to involve highly specialized surgeons and surgical instruments, due to the concentration of functionally eloquent neurological tissue and the likelihood of disturbing surrounding tissue. Often, however, large drilled skull openings and access tunnels are required for gaining surgical access to a central or deep location of a surgical site. Particularly in the case of a craniotomy, for example, removal of a tumor necessarily requires compromise of some brain tissue by purposefully or unintentionally retracting brain tissue for affording access to the targeted area. Nonetheless, it is beneficial to minimize application of pressure to brain tissue as mush as practicable to mitigate collateral effects of surgery.

Configurations herein are based, in part, on the observation that conventional neurosurgical techniques tend to exert force on adjacent tissue, potentially causing undesired collateral effects. Neurological tissue tends to be sensitive to pressure, therefore neurosurgical procedures strive to avoid disturbing adjacent tissue outside the surgical target. Particularly in brain surgery operations, such as a craniotomy, it can be problematic to leave surrounding tissues undisturbed.

Neuroendoscopic techniques are commonly used in many neurosurgical procedures and represent a minimally invasive surgical technique. The standard approach in this technique is insertion of an operating sheath and then introduction of the neuroendoscope (a particular type of endoscope) with a working channel for surgical instruments through this sheath. The first step of this approach is cannulating the ventricle (fluid spaces in the brain) with an introducer to maintain a passageway for an endoscope and related instruments. This can be accomplished with a peelaway catheter introducer or with a reusable rigid obturator/operating sheath. Both provide a passageway to repeatedly insert and withdraw the instruments and endoscope without any need to recannulate the tissue during the surgery. This technique is sufficient for many procedures but conventional introducers or obturator/operating sheaths have particular shortcomings and disadvantages.

Since the conventional sheaths are rigid tunnels with a fixed, small size (diameters 4-7 mm), working channels of operating sheaths accept only very small instruments (e.g. having diameters of approximately 1.7-2.8 mm). Therefore only very tiny pieces from the lesions, such as tumors, can be removed with these thin instruments during the procedures. Further, only one or two instruments can be used because of small size of the operating sheath, and no standard suction tube can be introduced for tumor suctioning. Usage of two or more instruments simultaneously is extremely difficult if not impossible, and if attempted, both instruments and the scope must remain parallel in the operating sheath throughout the procedure. Due to the small clearance, instruments cannot maneuver significantly without also moving the operating sheath. Maneuvers of the surgical instruments tend to force the rigid sheath to move with the instruments and push/retract the surrounding tissue which may cause undesired collateral effects such as tissue damage. Because of these limitations, endoscopic resection of some intraventricular solid/semi-solid lesions, such as tumor or colloid cysts, with endoscopic techniques becomes a very challenging procedure and may not be performed both quickly and safely.

Therefore, there is a need for a soft, non-rigid sheath which would provide a larger passageway to the ventricle to accommodate standard size surgical instruments such as suction tips, forceps, scissors, and coagulators, and generally, to use multiple instruments simultaneously and to allow maneuvers without significant retraction to surrounding tissue.

Unfortunately, conventional approaches suffer from the shortcoming that rigid access devices such as rigid sheaths impose constant pressure on the brain tissue as force from the sheath tends to displace brain tissue. Narrow access resulting from smaller diameter surgical access tunnels tends to limit instrument mobility in the surgical site, while larger drilled holes for accommodating a larger sheath compromise additional neurological tissue. Accordingly, configurations herein substantially overcome the shortcoming of displacement pressure, imposed by conventional rigid sheaths, by providing a flexible sheath that mitigates constant pressure on the brain tissue around the surgical tunnel. The flexible sheath as disclosed herein conforms to the surgical access tunnel while the tissue is at rest, and allows temporary deformation as the surgical instruments are manipulated while accessing the surgical site. Although the surgical instruments may need to be angled during the procedure, and thus exert force against the flexible sheath and corresponding adjacent tissue, such forces are temporary and not for the duration of the procedure.

In further detail configurations discussed further below disclose a surgical device including an obturator adapted for insertion through surgical tissue to a surgical site, and a plurality of rigid sheath portions disposed around the obturator, such the rigid sheath portions are in circumferential engagement around the obturator for defining a surgical passageway through the surgical tissue. Configurations herein employ a two part rigid sheath including an inner sheath portion and an outer sheath portion. A flexible sheath is adapted for insertion between the rigid sheath portions following withdrawal of the obturator, using an introducer or other mechanism for drawing the flexible sheath between the rigid sheath portions. The inserted flexible sheath is periodically deformable in response to biasing forces from surgical instruments, such that the periodic deformation relieves constant pressure on the surgical tissue. The plurality of rigid sheath portions are slideably removable following insertion of the flexible sheath. Installation of the flexible sheath invokes a method of providing surgical access that includes inserting an obturator assembly including an obturator disposed between the plurality of elongated, rigid sheath portions, such that the rigid sheath portions encase or encircle the obturator for defining a surgical passageway through surgical tissue. Following insertion, the surgeon withdraws the obturator, and inserts, in the defined surgical passageway, a flexible sheath having a resilient tubular shape of slightly smaller diameter than a drilled surgical channel that the obturator was extended through. The surgeon then withdraws each of the portions of the rigid sheath portions in succession, in which the rigid sheath portions are adapted to slideably pass between the flexible sheath and surgical tissue.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 2a-2e show the individual components of the sheath of FIG. 1;

DETAILED DESCRIPTION

Figure 1A:
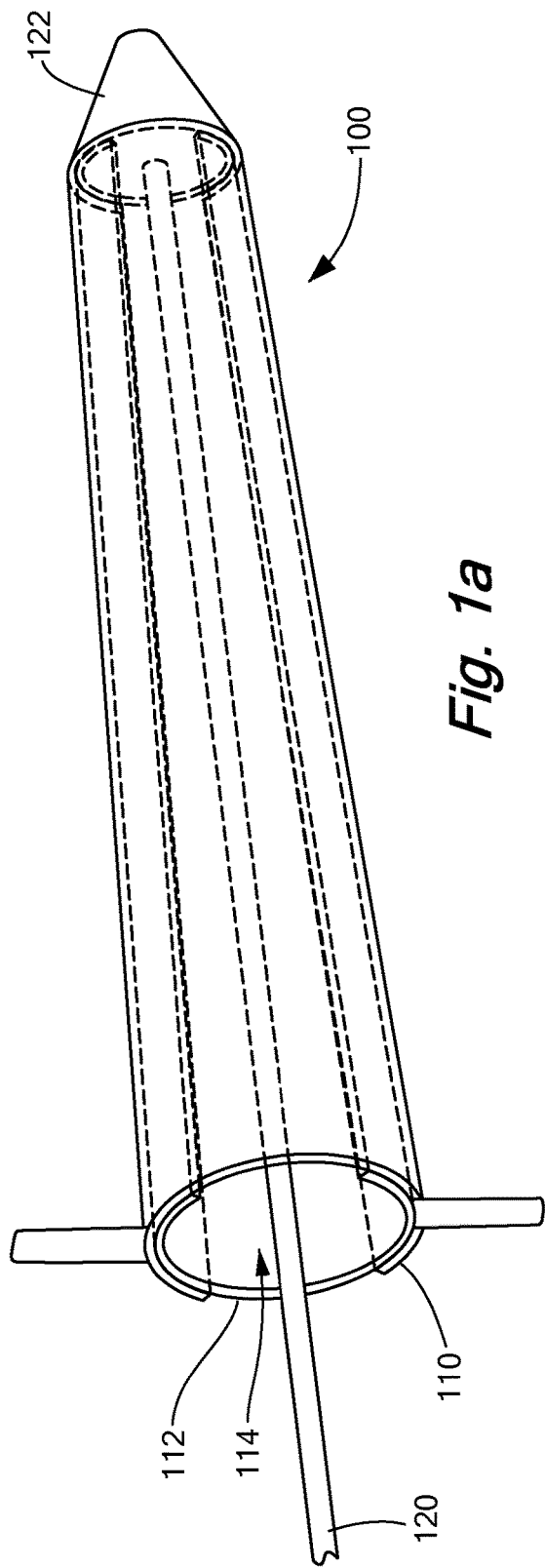
FIGS. 1a-1c show the assembled components of the flexible sheath and insertion mechanism.

Configurations disclosed herein relate to neuroendoscopic instruments and surgical techniques used in neurosurgical operations in human brains. It more particularly relates to the introducer/obturator/operating sheaths used in neuroendoscopic procedures to provide a passageway for inserting, withdrawing and reinserting the neuroendoscopes and surgical instruments during these procedures. The disclosed flexible sheath and method of insertion thereof includes three components: the outer sheath, obturator and inner/operating sheath, referred to herein as the flexible sheath. The outer sheath has at least two portions of slightly different diameters such that engage by sliding the smaller diameter inner sheath into the larger diameter outer sheath.

In contrast to conventional cannulated access, employing a unitary rigid sheath, the flexible sheath employs a multi-part rigid sheath for insertion. An obturator or other elongated insertion member drives a sheath assembly into a surgical tunnel or recess, typically a hole drilled through the skull and brain of the surgical patient. The inserted sheath assembly includes two or more rigid sheath portions disposed around the obturator. The individual rigid sheath portions engage or interlock to define a cannulated access channel through the drilled surgical tunnel. The obturator has a tapered or angled tip for guiding the sheath assembly through the surgical tunnel to a target region such as a ventricle or other brain structure for which surgical intervention is sought. Following insertion, the obturator is withdrawn and a flexible sheath inserted in the surgical tunnel defined by the rigid sheath portions. Alternatively, the flexible sheath may be inserted with the rigid sheath portions and the obturator subsequently withdrawn.

Configurations herein therefore disclose a flexible surgical sheath and multi-part insertion cannula, or rigid sheath, for inserting the flexible sheath in the surgical tunnel to gain access to a ventricle or other surgical target. Due to the flexibility of the sheath and the fragility of the surrounding brain tissue, insertion of a sheath assembly facilitates insertion of the flexible sheath into the drilled surgical tunnel, followed by withdrawal of the components of the sheath assembly, according to the method disclosed herein, leaving the flexible sheath in place for the duration of the surgical procedure. An optional depth limiter provides a substantially flush surface at a proximate end of the sheath nearest the skull surface for gauging depth into the surgical tunnel.

Configurations herein provide the following features to overcome the shortcomings of conventional neuroendoscopic techniques. The disclosed method provides a large passageway to intracranial fluid spaces, such as the ventricle, which may easily accommodate standard size neurosurgical instruments. Further, the larger passageway allows the surgeon to use multiple instruments simultaneously. The rigid outer sheath, defined by the inner and outer portions, is used only to introduce the flexible inner sheath and is then removed. The flexible inner sheath thereafter imposes little or no tension to surrounding brain tissue, facilitates maneuvers of the instruments, and allows the surgeon to use multiple instruments in non-parallel fashion, thus allowing an angled usage to enhance access, leverage etc. Further, the flexible sheath allows reorientation of the scope and/or instruments to side, up or down as needed by just changing the direction of the scope and/or instrument(s), and provides a safe passageway for repeated insertion and withdrawal of the scope and/or instruments. The usage of the flexible sheath therefore permits endoscopic instrument usage without injuring the surrounding brain tissue.

Figure 1C:
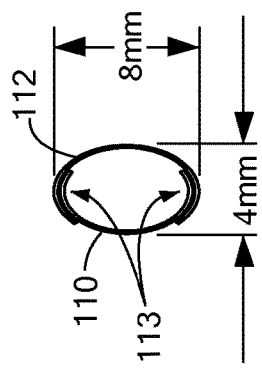
Figure 1B:
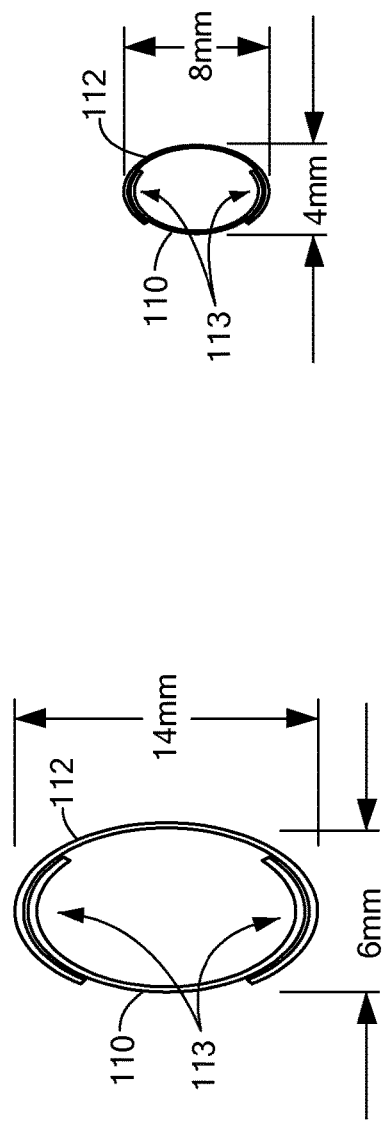
Figure 2C:
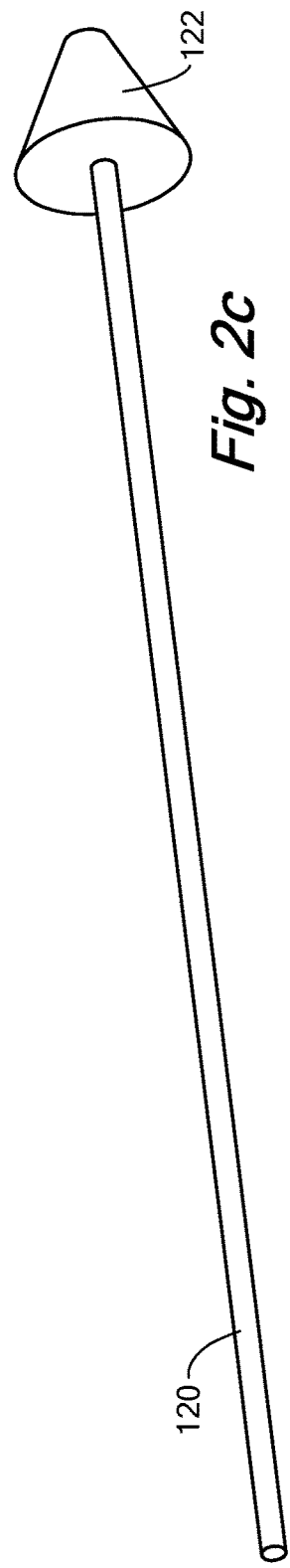
Figure 2D:
Figure 2E:
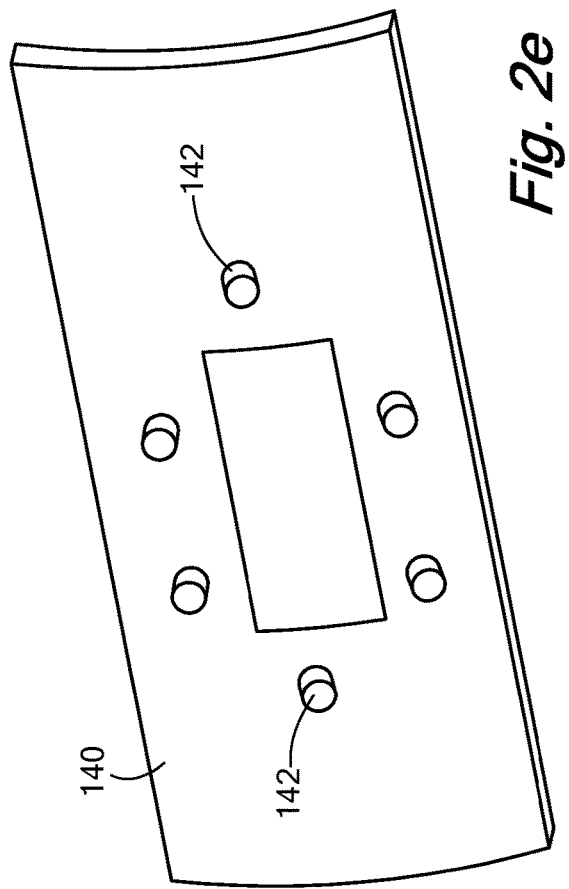

Following insertion, withdrawal of the obturator leaves the surgical tunnel defined by the rigid sheath portions flanking the flexible sheath. Subsequent removal of each of the rigid sheath portions leaves only the flexible sheath, thus eliminating the outward force exerted by the rigid sheath portions on the brain tissue. The brain tissue is therefore relaxed as the flexible sheath occupies the surgical tunnel, while allowing insertion of endoscopic surgical instruments through the flexible sheath. FIGS. 1a-1c show the assembled components of the flexible sheath and insertion mechanism adapted for insertion into a surgical tunnel (150, FIG. 4b, below). The surgical tunnel may be formed by any suitable means, such as drilling, and has a size based on the sheath assembly. Referring to FIGS. 1a-1c, the sheath assembly 100 includes two rigid sheath portions, including an inner sheath portion 110 and an outer sheath portion 112 disposed around an obturator 120 having a tip 122. Referring also to FIGS. 2a-2b, the inner 110 and outer 112 sheath portions (inner sheath 110 and outer sheath 112, hereinafter) define an insertion void 114 approximating the diameter of the surgical tunnel. The insertion void 114 is defined by the rigid inner and outer sheaths 110, 112 and is adapted to receive the flexible sheath 130 of FIG. 2d, discussed further below.

FIGS. 1b and 1c show engagement of the inner and outer rigid sheaths 110, 112 of particular sizes. A generally oblong or oval arrangement tends to provide greater mobility, and may be 6 mm*14 mm, as shown in FIG. 1b, or 4 mm*8 mm as shown in FIG. 1c, if a smaller surgical tunnel is sufficient. The inner 110 and outer 112 sheaths will be in different lengths, typically increments of 3, 4, 5 and 6 cm are most likely for typical applications. As shown in FIGS. 1b and 1c, the inner sheath 110 has a slightly smaller diameter and extends a lesser arcuate distance than the outer sheath 112, which has a larger diameter. The inner 110 and outer 112 sheaths overlap in an overlap region 113, which secures the inner 110 and outer sheaths 112 in a slideable axial engagement for allowing withdrawal while maintaining a continuous supportive encircling around the flexible sheath 130 from the overlap region 113.

FIGS. 2a-2e show the individual components of the sheath of FIG. 1. The inner sheath 110 has a slightly smaller elliptical diameter than the outer sheath 112 for insertion thereof. Further, the inner 110 and outer sheaths 112 may be tapered toward a distal end 116, 118 that is inserted into a surgical tunnel. The inner 110 and outer sheaths 112 may be any suitable corresponding shape, such as elliptical, oblong or circular, however, an elliptical configuration is shown herein as an example. In the example of FIGS. 2a-2e, the distal ends 116, 118 have a diameter 142 and 146 respectively, which may be slightly smaller than a diameter 141, 145 of proximate ends 115 and 117. An opening 143, 147 in the annular surface of the inner 110 and outer sheaths 112 allows slideable communication while maintaining continuous support encircling the flexible sheath because of the overlap region 113. Once positioned, a depth limiter 140, substantially flush with the surgical tunnel opening on the skull, may secure the flexible sheath 130 by tabs or slots 142, and provides a reference working surface for gauging depth within the surgical tunnel 150 and provides protection to tissue and bone structures around the opening of the surgical tunnel. Winglike protrusions or handles 148 on the inner and outer sheaths facilitate removal, as discussed below with respect to FIGS. 4a-4k.

Figure 3:
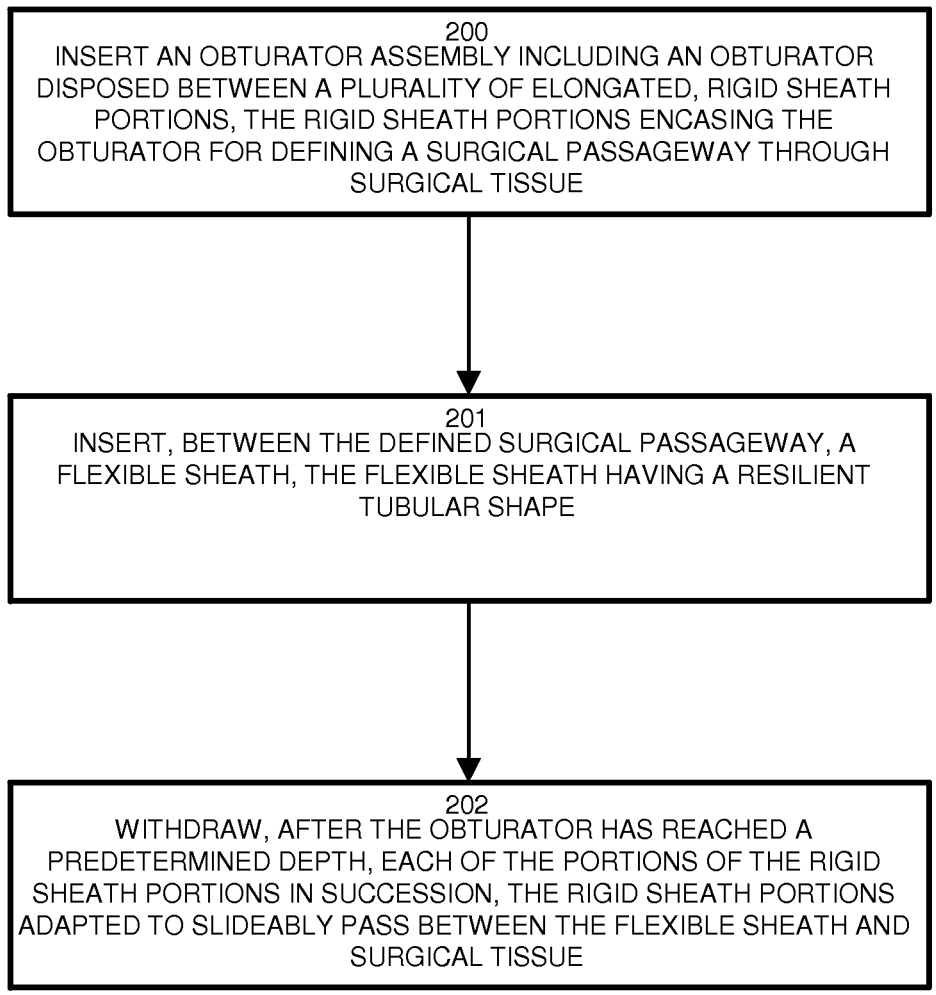
FIG. 3 is a flowchart of a method of installing the flexible sheath of FIG. 1.

FIG. 3 shows a method of installing the flexible sheath. Referring to FIG. 3, at step 200, the method of providing surgical access comprising as disclosed herein includes inserting an obturator (sheath) assembly 100 having an obturator 120 disposed between a plurality of elongated, rigid sheath portions 110, 112, in which the rigid sheath portions encase or surround the obturator 120 for defining a surgical passageway through surgical tissue. A surgeon inserts, between the defined surgical passageway, the flexible sheath 130, in which the flexible sheath 130 has a resilient tubular shape receptive to endoscopic instruments, as depicted at step 201. The obturator 120 may also be also used for placement of surgical support devices, such as for mounting neuronavigator system sensors. Typically, the obturator is inserted to a depth based on the surgical target (i.e. ventricle), following which the obturator is withdrawn and the flexible sheath 130 inserted with the same obturator 120 or with an introducer. Both the rigid insertion cannula (inner 110 and outer 112 sheath portions) and the obturator 120 will have depth markings for gauging insertion. Alternatively, the flexible sheath may accompany the insertion assembly if the obturator may be withdrawn inside of it. After the obturator 120 has reached a predetermined depth, the surgeon withdraws the obturator and each of the portions of the rigid sheath portions 110, 112 in succession, in which the rigid sheath portions 110, 112 are adapted to slideably pass between the flexible sheath 130 and surgical tissue, as shown at step 202. The flexible sheath 130 remains disposed in the surgical tunnel 150 for providing surgical access without exerting constant pressure on the surrounding tissue as conventional, unitary rigid catheters do.

Figure 4A:
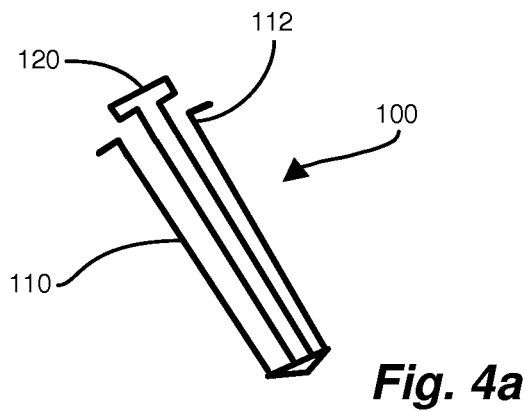
FIGS. 4a-4k show a method of inserting the flexible sheath of FIGS. 1a-2e.
Figure 4B:
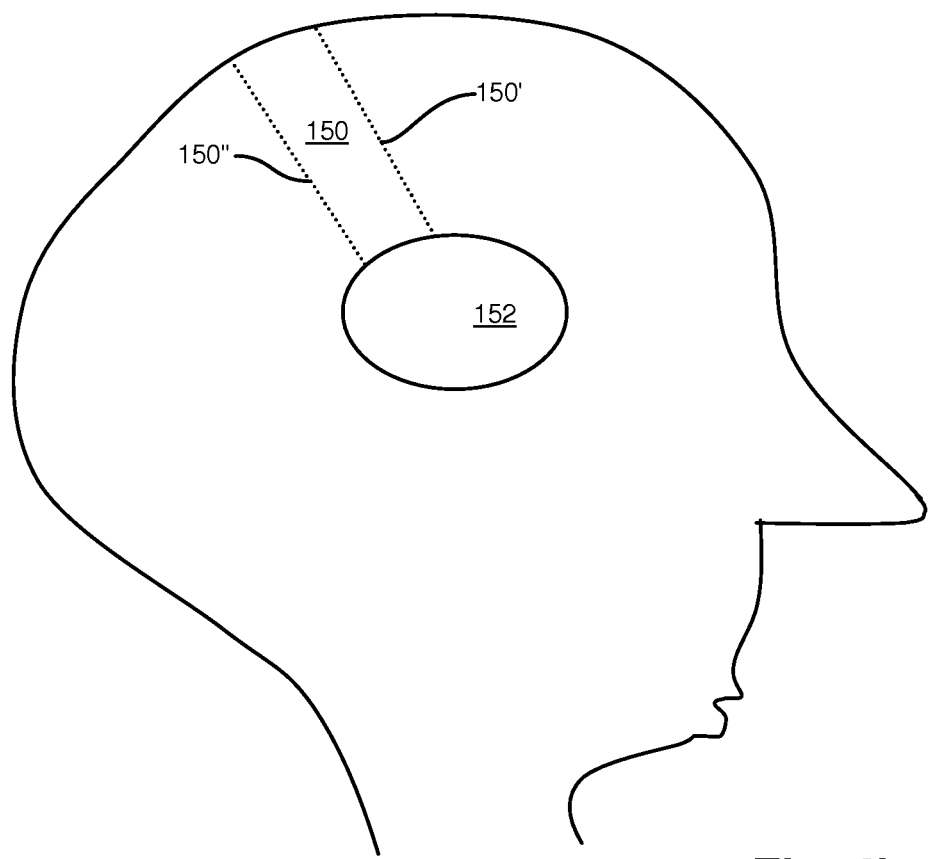
Figure 4C:
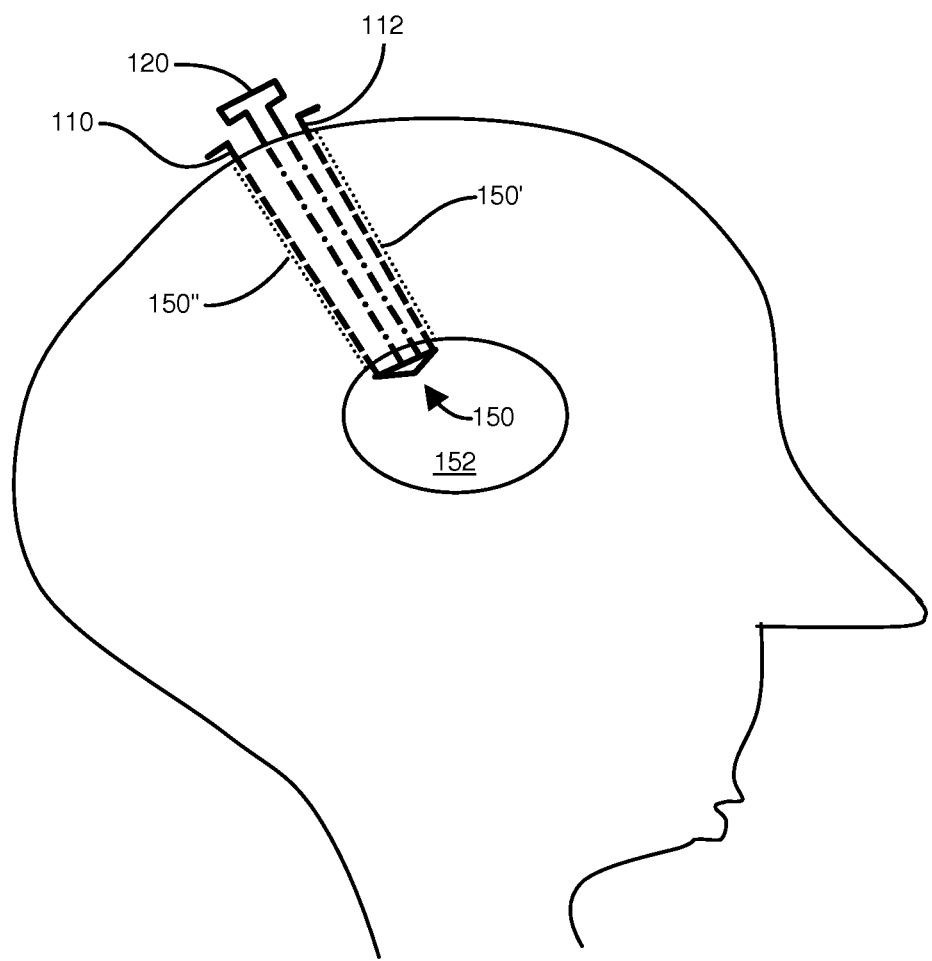

FIGS. 4a-4k show a method of inserting the flexible sheath of FIGS. 1 and 2. Referring to FIG. 4a, the sheath assembly 100 is shown in a cutaway view. In FIG. 4b, the sheath assembly 100 is inserted into the surgical tunnel 150, having walls shown by dotted lines 150', 150", by the surgeon via the obturator 120. In a typically craniotomy, a fluid space defined by a ventricle 152 represents a desired insertion depth for accessing a surgical target. Insertion of the sheath assembly 100 in FIG. 4c disposes the inner sheath 110, outer sheath 112 and obturator 120 in the surgical tunnel 150 as a single unit.

Figure 4D:
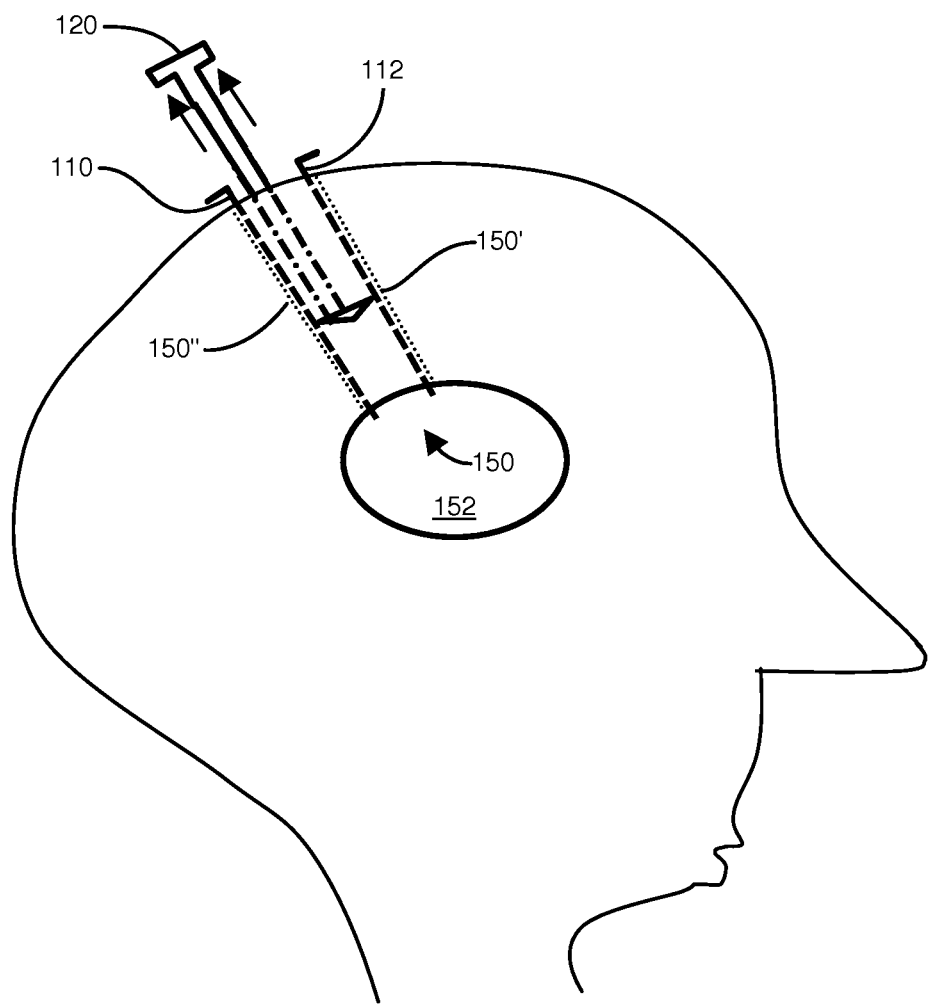
Figure 4E:
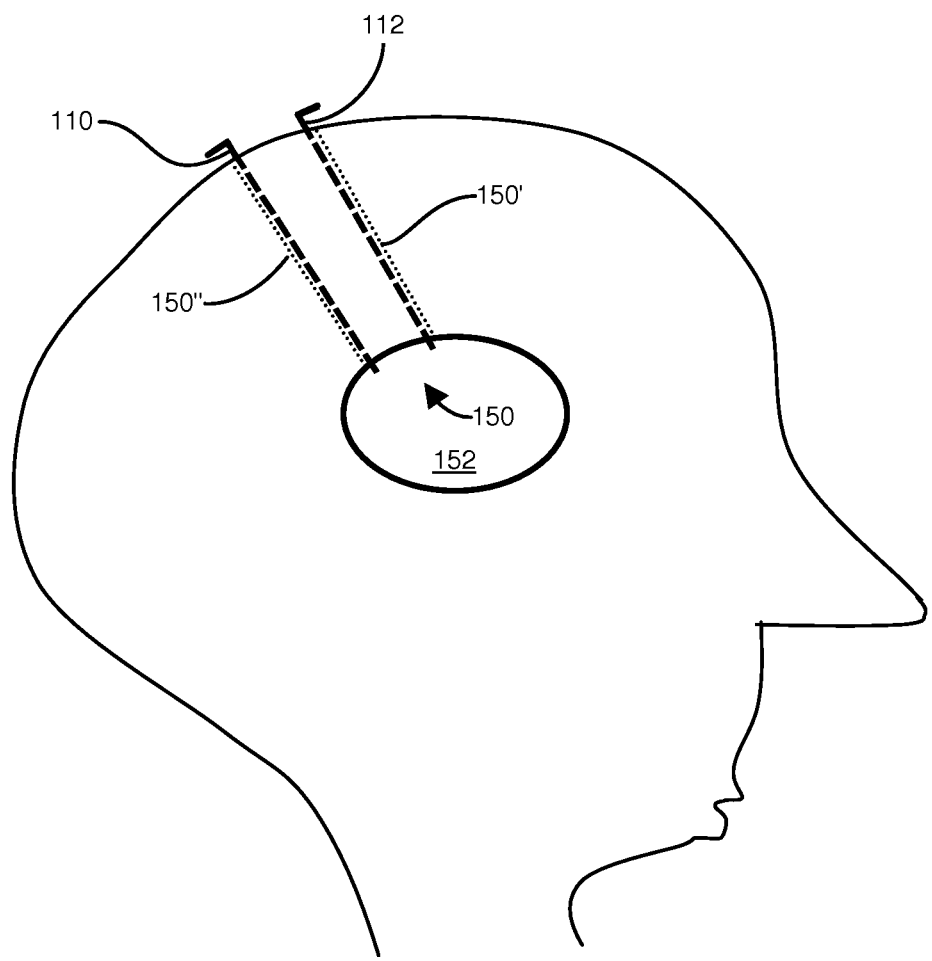
Figure 4F:
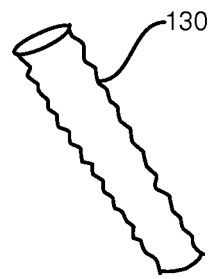
Figure 4G:
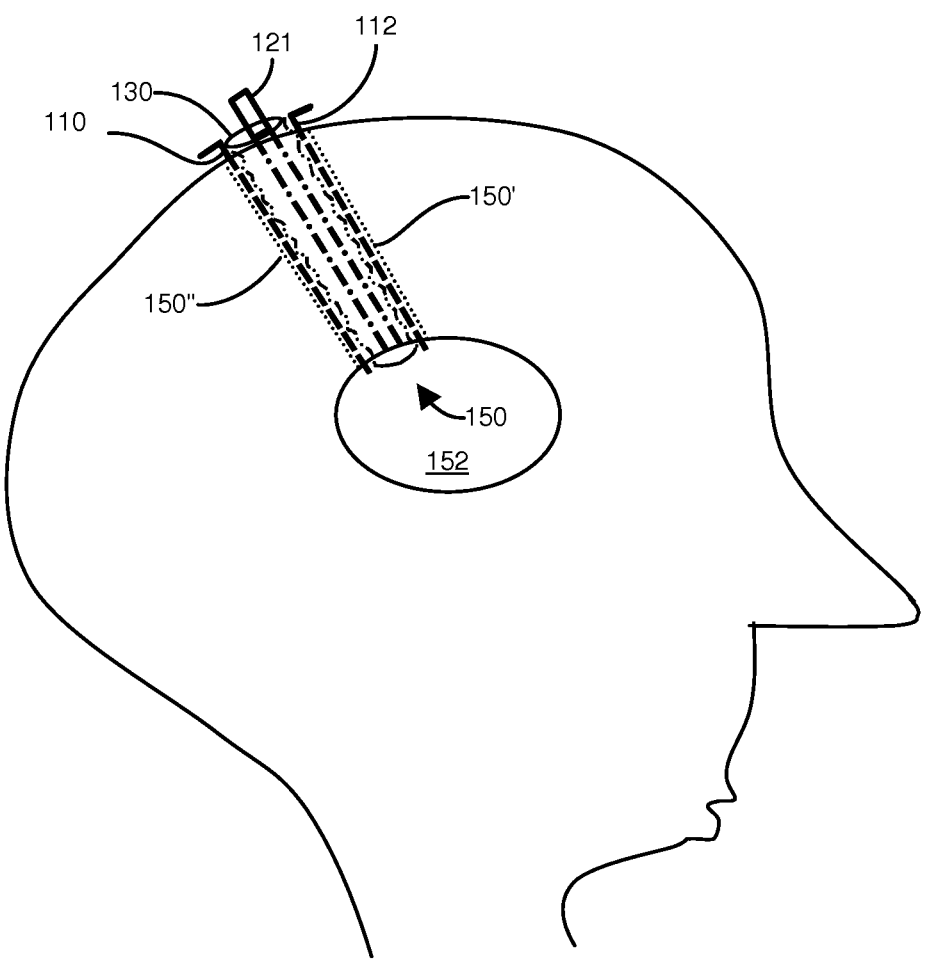
Figure 4H:
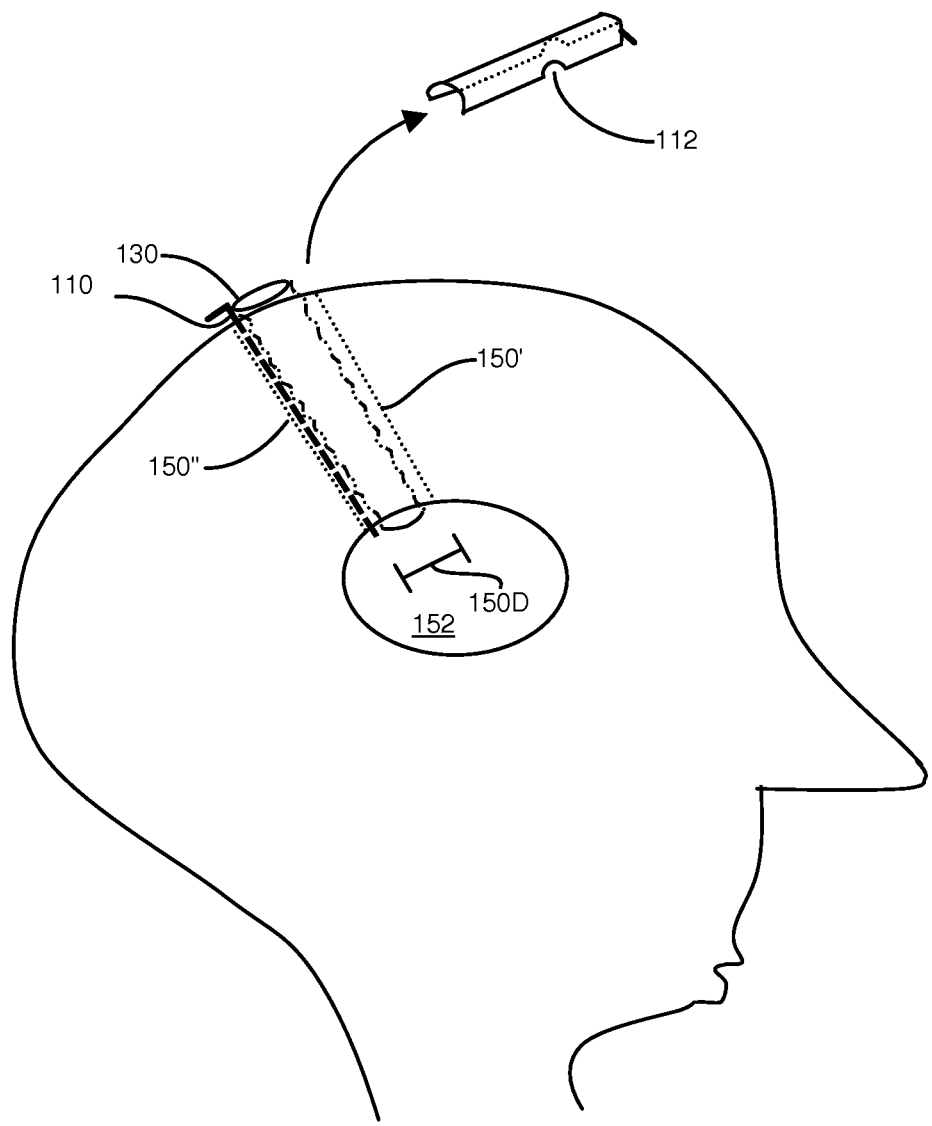
Figure 4I:
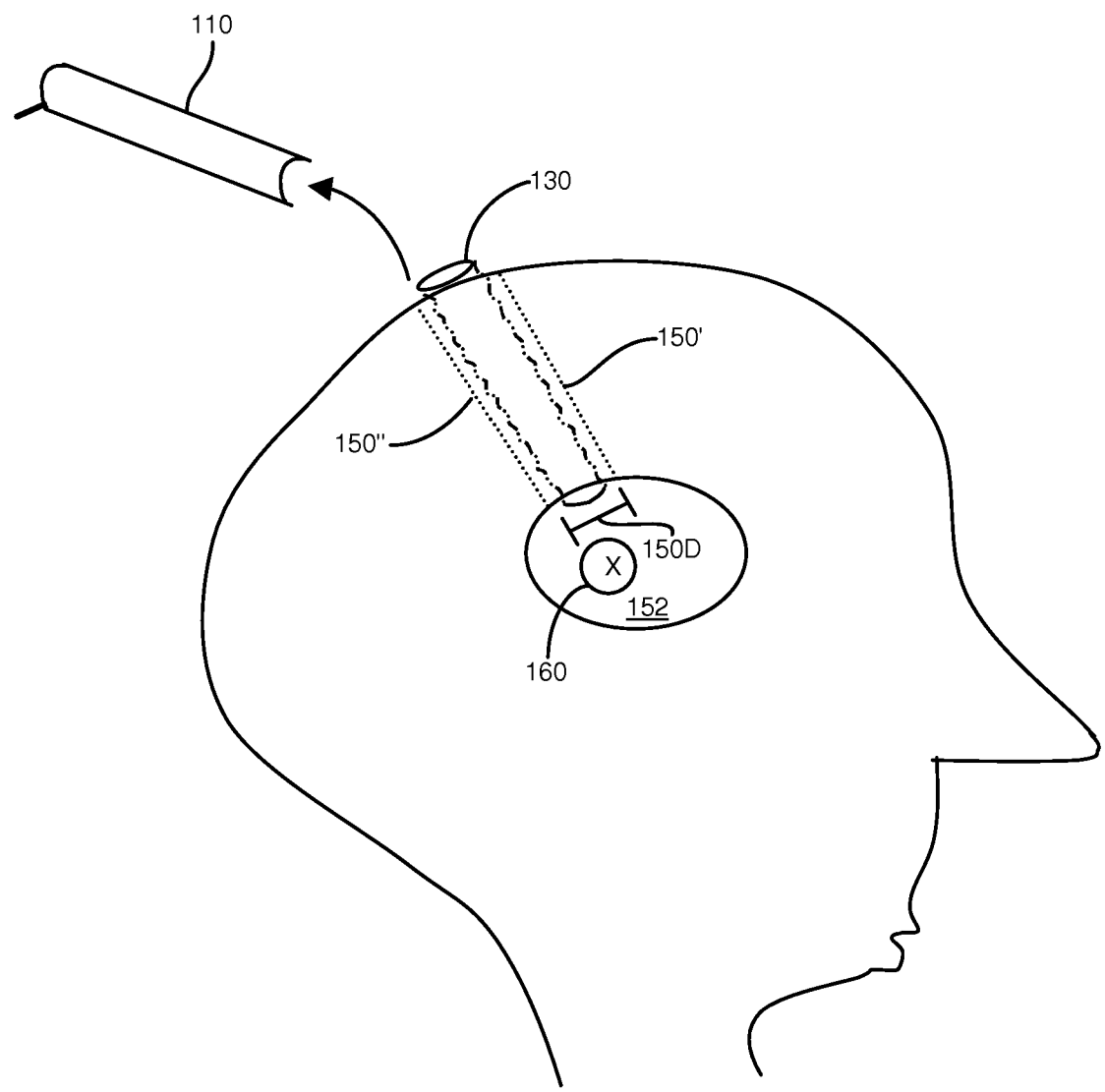
Figure 4J:
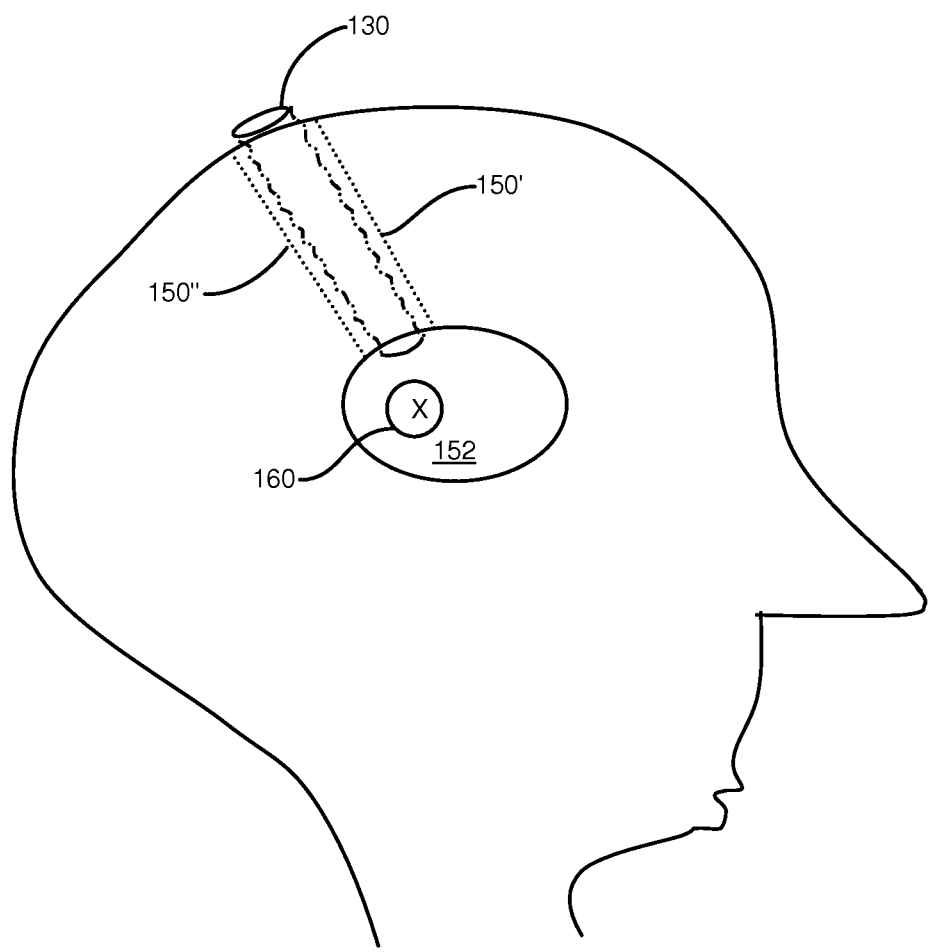
Figure 4K:
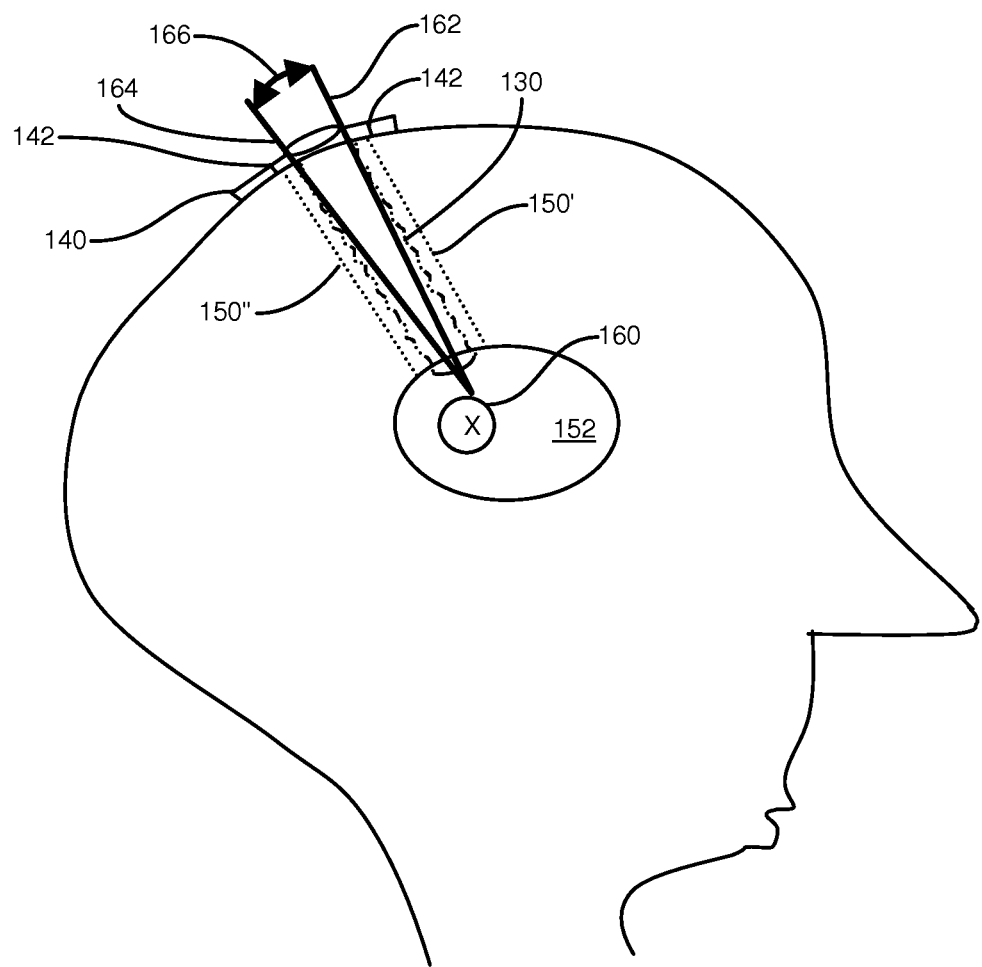

Referring to FIGS. 4b-4j, once the sheath assembly 100 is positioned, the surgeon withdraws the obturator 120 in FIG. 4d, leaving the inner 110 and outer sheaths 112 within the surgical tunnel 150 in FIG. 4e. The flexible sheath 130 of FIG. 4f is inserted using an introducer or bayonet 121 in FIG. 4g. The outer sheath 112 is then removed from the surgical tunnel 150 in FIG. 4h, leaving the flexible sheath 130 frictionally engaged between the walls 150' of the surgical tunnel 150 and the inner sheath 110. A diameter 150D of the surgical tunnel will tend to decrease as the rigid outer sheath 112 is removed and relieves pressure exerted on it against the wall 150' of the surgical tunnel 150. FIG. 4i shows the corresponding removal of the inner sheath 110 and subsequent further contraction of the surgical tunnel 150 around the flexible sheath 130, leaving only the flexible sheath 130 in the surgical tunnel 150 (FIG. 4j). Removal order of the inner 110 and outer sheaths 112 may be varied; since the outer sheath 112 has greater surface area, it is beneficial to remove first so as to slide past the inner sheath 110 rather than have the entire surface area of the outer sheath 112 frictionally engage the flexible sheath 130, to minimize the chance of drawing the flexible sheath 130 out of the surgical tunnel 150. Removal of the sheaths 110, 112 permits access to a surgical site 160, such as a tumor, with instruments, as shown in FIG. 4k. Surgical instruments 162, 164 may then be employed to access the surgical site 160. An insertion angle 166 is facilitated by the diameter 150D of the surgical tunnel, and the flexible sheath 130 allows a greater insertion angle 166 by permitting a range of motion to temporarily compress the flexible sheath 130 against the tunnel walls 150', 150". Such temporary pressure subsides with instrument repositioning, in contrast to a fixed rigid sheath that exerts constant pressure. FIG. 4k also shows an optional depth limiter 140, which may be applied at any time for maintaining a known working surface and for anchoring the flexible sheath 130 via slots or tabs 142.

Figure 5:
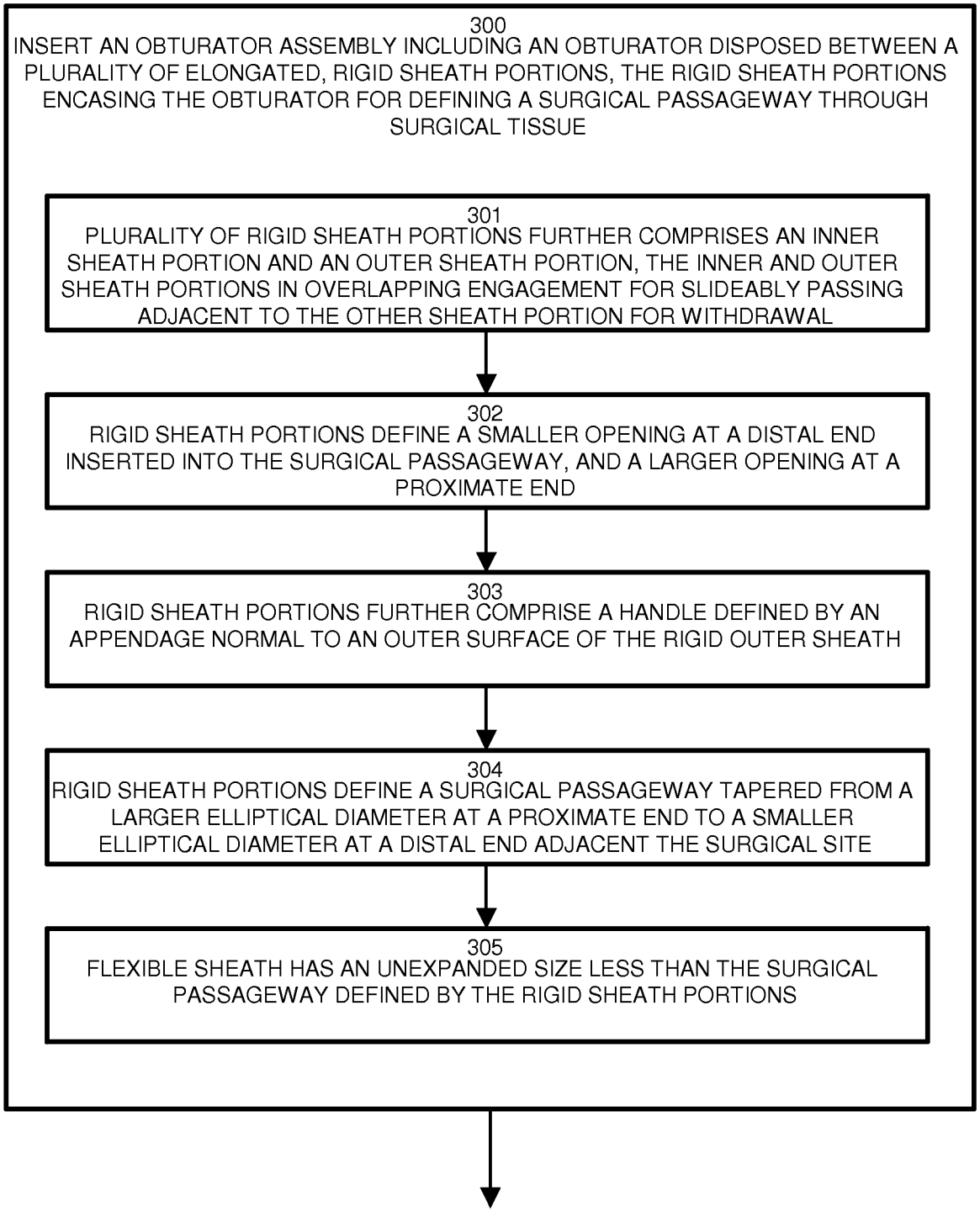
FIGS. 5 and 6 describe a method of employing the flexible sheath in a surgical procedure as in FIGS. 4a-4k.
Figure 6:
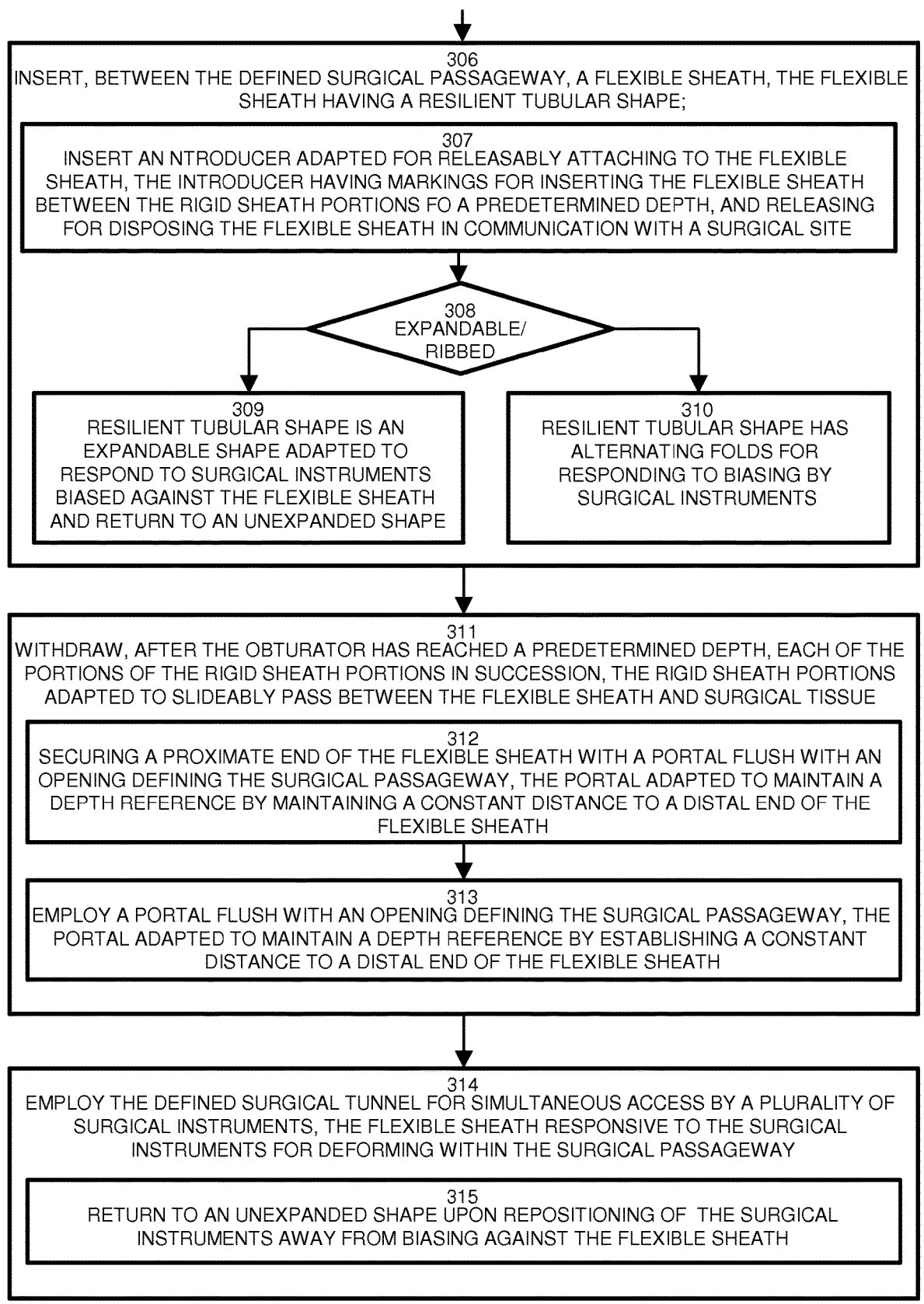

FIGS. 5 and 6 describe a method of employing the flexible sheath in a surgical procedure as in FIGS. 4a-4k. Referring to FIGS. 5 and 6, and continuing to refer to FIGS. 1 and 4, at step 300, the method of providing surgical access via the flexible sheath includes inserting an obturator or sheath assembly 100 including an obturator 120 disposed between a plurality of elongated, rigid sheath portions 110, 112 encasing the obturator 120 for defining a surgical passageway or tunnel 150 through surgical tissue. In the example arrangement shown, the plurality of rigid sheath portions includes an inner sheath 110 portion and an outer sheath portion 112, such that the inner and outer sheath portions are in overlapping engagement for slideably passing adjacent to the other sheath portion for withdrawal, as shown at step 301. The rigid sheath portions 110, 112 may be tapered such that the rigid sheath portions define a smaller opening at a distal end 116, 118 inserted into the surgical passageway, and a larger opening at a proximate end 141, 145, as shown at step 302. The rigid sheath portions 110, 112 may further comprise a handle 148 defined by an appendage normal to an outer surface of the rigid sheath portions 110, 112, as depicted at step 303. The rigid sheath portions 110, 112 therefore define a surgical passageway (tunnel 150) tapered from a larger elliptical diameter at a proximate end to a smaller elliptical diameter at a distal end adjacent the surgical site, as shown at step 304. Alternatively, a variety of circular or oblong tunnels may be employed. Generally, the flexible sheath 130 has an unexpanded size less than the surgical passageway defined by the rigid sheath portions 110, 112, as depicted at step 305 so as to be disposed easily into the surgical tunnel 150 following retraction of the rigid sheath portions 110, 112.

Once the obturator 120 is retracted (FIG. 4d), the surgeon inserts, within the defined surgical passageway 150, a flexible sheath 130 having a resilient tubular shape, as depicted at step 306 and shown in FIG. 4e. This may further employ an introducer or bayonet 121 adapted for releasably attaching to the flexible sheath 130, such that the introducer 121 has markings for inserting the flexible sheath 130 between the rigid sheath 110, 112 portions to a predetermined depth, and releasing the flexible sheath 130 for disposing the flexible sheath 130 in communication with a surgical site 160, as shown at step 307.

Figure 7A:
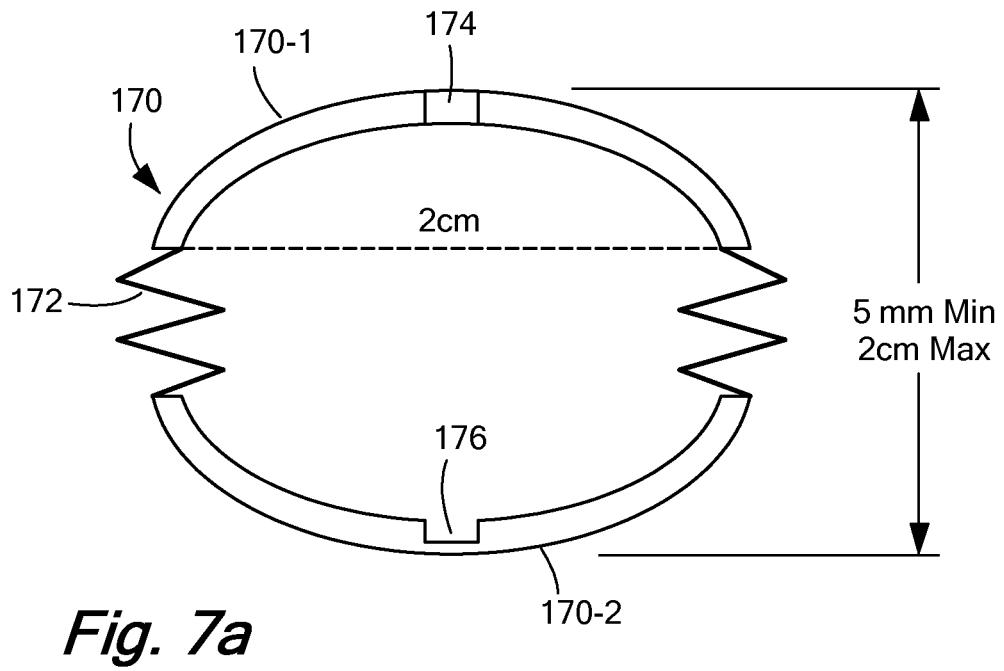
FIGS. 7a-7f shown an alternate single piece sheath configuration.
Figure 7B:
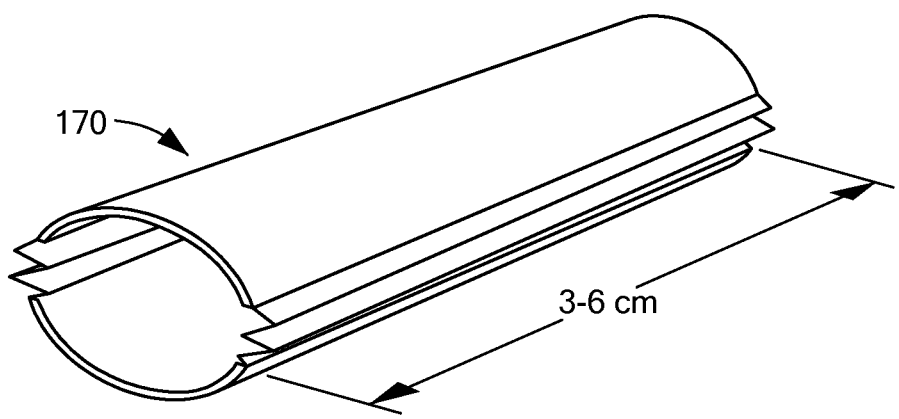
Figure 7C:
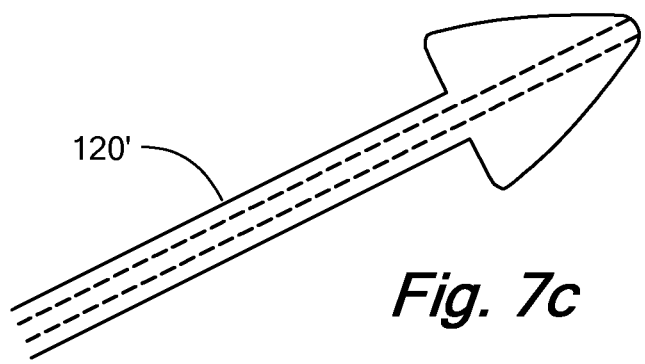
Figure 7D:
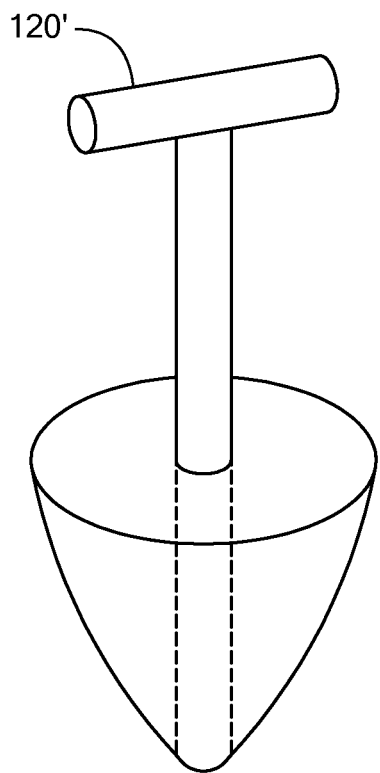

The flexible sheath may be of any suitable construction, such as expandable or ribbed, as shown at step 308. Therefore, the resilient tubular shape may be an expandable shape adapted to respond to surgical instruments biased against the flexible sheath and return to an unexpanded shape, as shown at step 309. Alternatively, the resilient tubular shape may have alternating folds for responding to biasing by surgical instruments 162, 164 as shown step 310 and below in FIGS. 7a, 7b.

After the obturator 120 has reached and defined a predetermined depth, and been subsequently withdrawn, each of the portions of the rigid sheath portions 110, 112 are withdrawn in succession, in which the rigid sheath portions 110, 112 are adapted to slideably pass between the flexible sheath 130 and surgical tissue, as shown at step 311 and in FIGS. 4h and 4i. The procedure may further include securing a proximate end of the flexible sheath 130 with a portal such as a depth limiter 140 flush with an opening defining the surgical passageway, as depicted at step 312, such that the portal is adapted to maintain a depth reference by maintaining a constant distance to a distal end of the flexible sheath 130. The depth limiter 140 is flush with an opening defining the surgical passageway, and thus is adapted to maintain a depth reference by establishing a constant distance to a distal end of the flexible sheath 130, as depicted at step 313.

Following insertion of the flexible sheath 130, the surgeon employs the defined surgical tunnel 150 for simultaneous access by a plurality of surgical instruments 162 and 164, such that the flexible sheath 130 is responsive to the surgical instruments 162, 164 for deforming within the surgical passageway, as depicted at step 314. The flexible sheath 130 then returns to an unexpanded shape upon repositioning of the surgical instruments 162, 164 away from biasing against the flexible sheath, as disclosed at step 315.

Figure 7F:
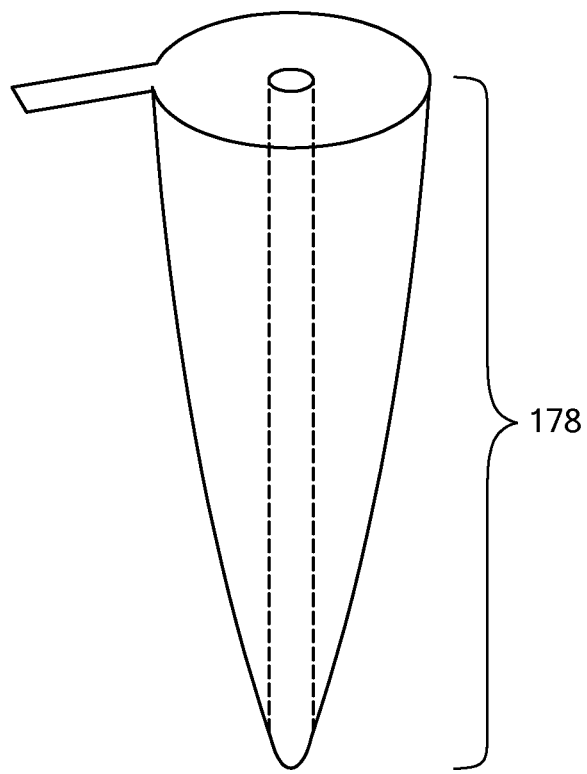
Figure 7E:
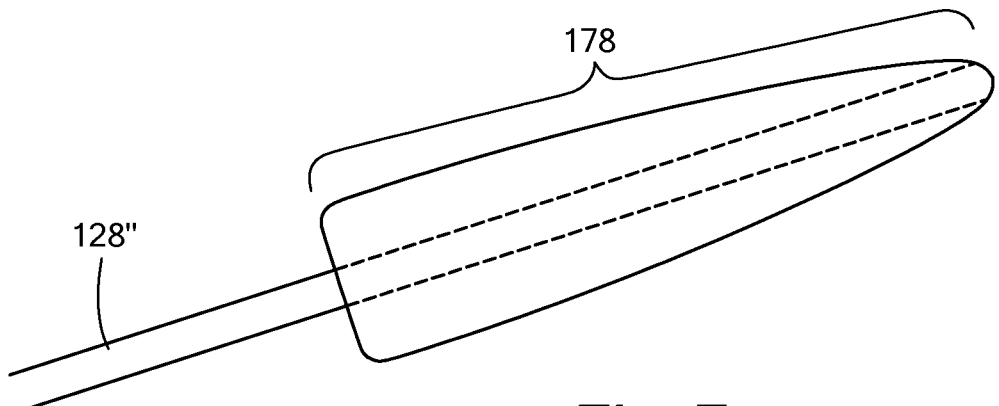

FIGS. 7a-7f shown an alternate single piece sheath configuration. Referring to FIGS. 7a-f, a fan fold configuration 170 employs alternately folded portions 172 for permitting expansion and retraction of the sheath 170. Each of rigid sides 170-1 and 170-2 are coupled by the folding portions 172. An irrigation channel 174 occupies one of the rigid sides 170-1, and an endoscope channel 176 occupies the opposed rigid side 170-2. Alternate arrangements for the obturator include obturator 120', and obturator 120" having an elongated tip 178, as shown in FIGS. 7e and 7f.

Figure 8A:
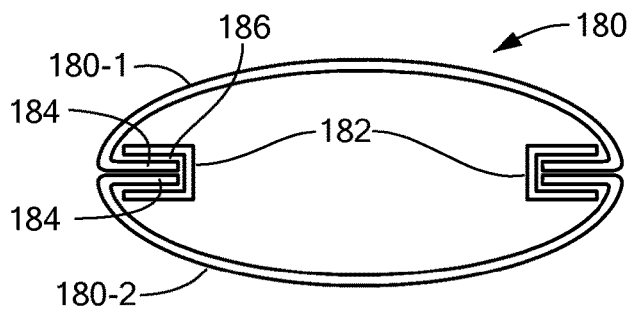
FIGS. 8a-8h show alternate linkage arrangements of the sheath portions.
Figure 8B:
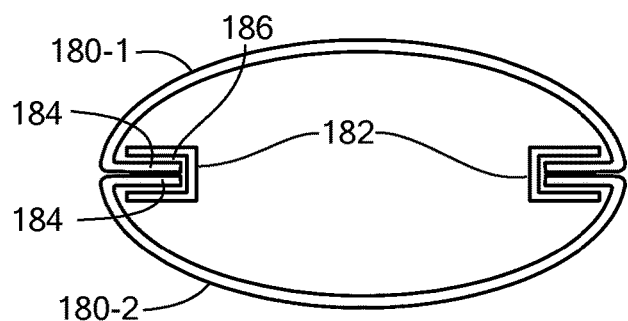
Figure 8C:
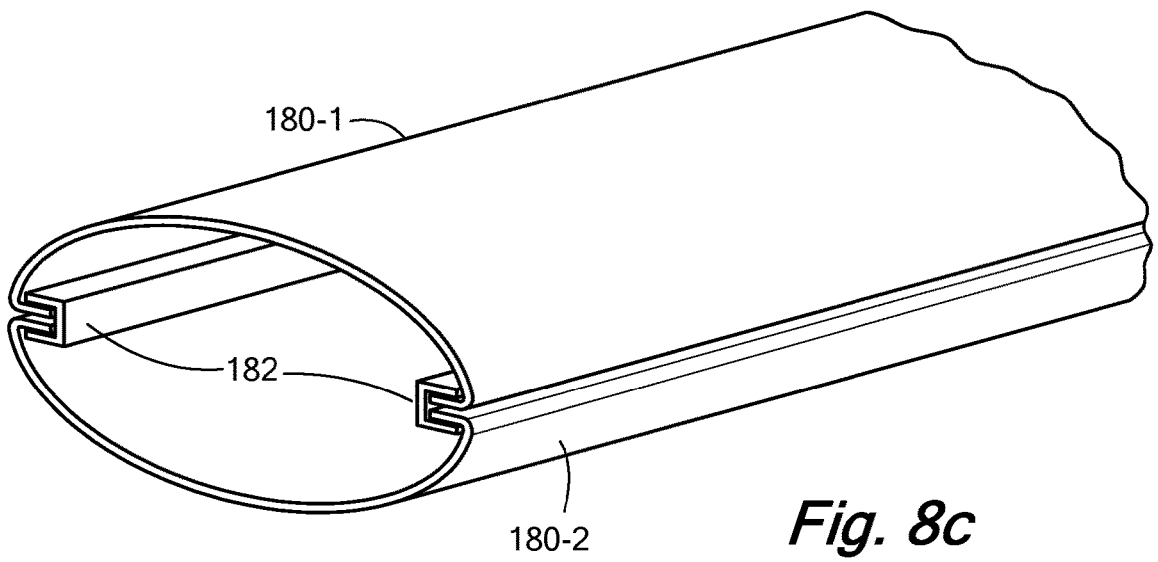
Figure 8D:
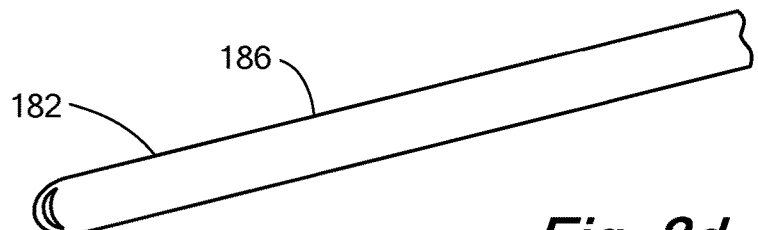
Figure 8E:
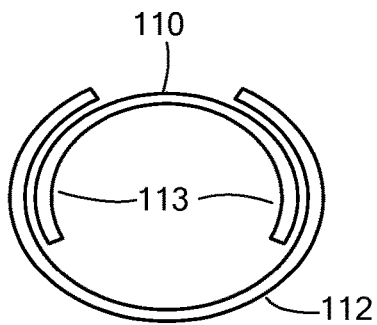
Figure 8F:
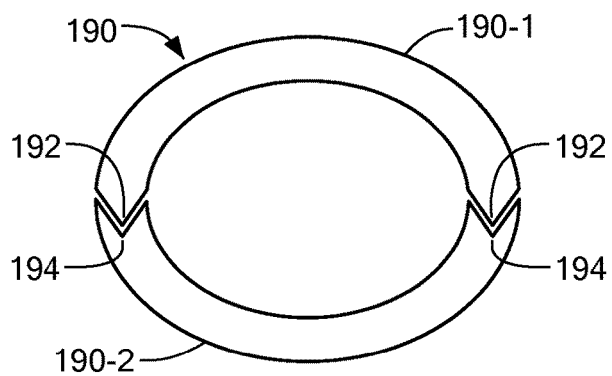
Figure 8G:
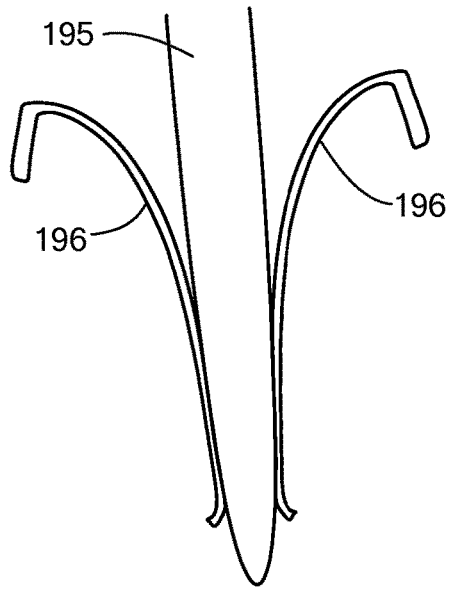
Figure 8H:
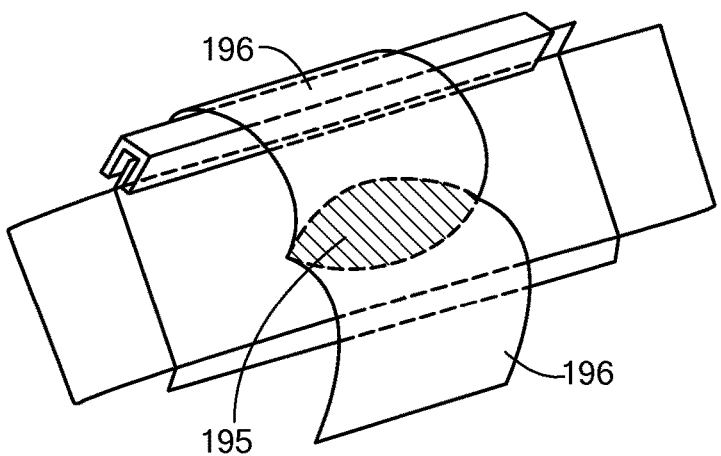

FIGS. 8a-8h show alternate linkage arrangements of the sheath portions 110 and 112. FIGS. 8a-8d show a flap and spine linkage including a rigid spine 182 having a slot 186. Each of rigid halves 180-1 and 180-2 has a flap 184, such that opposed flaps are engaged by the slot 186 of the spine 182 to couple the halves 180-1, 180-2. FIG. 8e shows a cross section view of the overlap region 113 of the configuration of FIG. 1 above. FIG. 8f shows a tongue and groove configuration 190 where each of portions 190-1 and 190-2 are linked by a tongue 192 adapted to be received by a groove or slot 194. FIGS. 8g and 8h disclose a peel away cannula 195 that employs tape-like peel away membranes 196 for installing the rigid sheath.

While the apparatus and methods defined herein have been particularly shown and described with references to embodiments thereof, it will be understood by those skilled in the art that various changes in form and details may be made therein without departing from the scope of the invention encompassed by the appended claims.

What is claimed is:

1. A surgical device consisting of:
   an obturator adapted for insertion through surgical tissue to a surgical site;
   a plurality of rigid sheath portions disposed around the obturator, the rigid sheath portions in circumferential engagement around the obturator for defining a surgical passageway through the surgical tissue, the plurality of rigid sheath portions further comprising an inner sheath portion and an outer sheath portion, the inner and outer sheath portions in overlapping engagement defining a circular insertion void; and
   a flexible sheath adapted for insertion into the circular insertion void defined by the engaged inner and outer sheath portions following withdrawal of the obturator, with both of the inner and outer rigid sheath portions being disposed between the inserted flexible sheath and the surgical tissue,
   wherein the flexible sheath is configured to be periodically deformable in response to biasing forces from surgical instruments, the periodic deformation relieving constant pressure on the surgical tissue, and
   the plurality of rigid sheath portions are adapted for axial withdrawal, passing between the flexible sheath and the surgical tissue, from the surgical passageway for separation from the flexible sheath following insertion of the flexible sheath.

2. The device of claim 1 wherein the flexible sheath has an unexpanded size less than the surgical passageway defined by the rigid sheath portions.

3. The device of claim 1 wherein the rigid sheath portions define a surgical passageway tapered from a larger diameter at a proximate end to a smaller diameter at a distal end adjacent the surgical site.

4. The device of claim 1 wherein the rigid sheath portions are adapted for slideable withdrawal, the rigid sheath portions maintaining a diameter of the surgical passageway during withdrawal.

5. The device of claim 1 wherein the flexible sheath has a diameter adapted for slideable insertion into the circular insertion void defined by the engaged inner and outer sheath portions.

6. The device of claim 1 wherein the plurality of rigid sheath portions are circular.

7. The device of claim 1 wherein the plurality of rigid sheath portions are oblong.

8. The device of claim 1 wherein the plurality of rigid sheath portions are elliptical.

9. The device of claim 1 wherein the plurality of rigid sheath portions are tapered toward a distal end.

10. A surgical device comprising:
    an obturator adapted for insertion through surgical tissue to a surgical site;
    a plurality of rigid sheath portions disposed around the obturator, the rigid sheath portions in circumferential engagement around the obturator for defining a surgical passageway through the surgical tissue, the plurality of rigid sheath portions further comprising an inner sheath portion and an outer sheath portion, the inner and outer sheath portions in overlapping engagement defining a circular insertion void; and
    a flexible sheath adapted for insertion into the circular insertion void defined by the engaged inner and outer sheath portions following withdrawal of the obturator, with both of the inner and outer rigid sheath portions being disposed between the inserted flexible sheath and the surgical tissue,
    wherein the diameters of the inner rigid sheath portion and the outer rigid sheath portion at the distal end are smaller than the diameters of the inner rigid sheath portion and the outer rigid sheath portion at the proximal end,
    the flexible sheath is configured to be periodically deformable in response to biasing forces from surgical instruments, the periodic deformation relieving constant pressure on the surgical tissue, and
    the plurality of rigid sheath portions are adapted for axial withdrawal, passing between the flexible sheath and the surgical tissue, from the surgical passageway for separation from the flexible sheath following insertion of the flexible sheath,
    wherein the inner rigid sheath portion and the outer rigid sheath portion are oblong or elliptical.

* * * * *